United States Patent [19]

Pelzer et al.

[11] Patent Number: 4,915,945

[45] Date of Patent: Apr. 10, 1990

[54] PROCESS FOR THE PREPARATION OF THE C1 INACTIVATOR

[75] Inventors: Hermann Pelzer; Helmut Heber; Norbert Heimburger; Hans M. Preis; Horst Naumann, all of Marburg, Fed. Rep. of Germany

[73] Assignee: Behringwerke Aktiengesellschaft, Marburg, Fed. Rep. of Germany

[21] Appl. No.: 724,050

[22] Filed: Apr. 18, 1985

Related U.S. Application Data

[63] Continuation of Ser. No. 518,101, Jul. 28, 1983, abandoned.

[30] Foreign Application Priority Data

Jul. 30, 1982 [DE] Fed. Rep. of Germany ....... 3228502

[51] Int. Cl.$^4$ .......................... A61K 37/02; C07K 3/20
[52] U.S. Cl. ......................................... 421/101; 514/8; 530/380; 530/417; 435/236
[58] Field of Search ............................. 514/8; 424/101; 435/236; 530/380, 417

[56] References Cited

FOREIGN PATENT DOCUMENTS 35204 9/1981 European Pat. Off. .

OTHER PUBLICATIONS

Pharmacia Fine Chemicals Catalogue, p. 3, Dec. 1977.
Reboul et al., FEBS Letters, vol. 79, No. 1, Jul. 1977, "A Simplified Procedure for the Purification . . . ".
Breitenbach, cited in Chem. Abstracts, vol. 90, No. 50792p.
Ochoa et al., cited in Chem. Abstracts, vol. 90, No. 150130q, 1979.

Primary Examiner—Jacqueline M. Stone
Attorney, Agent, or Firm—Finnegan, Henderson, Farabow, Garrett and Dunner

[57] ABSTRACT

The invention relates to a process for the preparation of C1 inactivator, which, if appropriate, is hepatitis-free and, if appropriate, can be lyophilized, and its use as a medicament.

18 Claims, No Drawings

PROCESS FOR THE PREPARATION OF THE C1 INACTIVATOR

This application is a continuation of application Ser. No. 518,101, filed July 28, 1983, now abandoned.

The invention relates to the preparation of a protein called the C1 inactivator and its use as a medicament.

The C1 inactivator, called after its property of inactivating C1 esterase in the complement system, additionally also "controls" important enzymes for the clotting of blood, especially in the contact phase, that is to say prekallikrein and factors XI and XII, as well as plasmin. On the basis of this specificity, the C1 inactivator has a particular physiological function. In general, it can be said that it is consumed when blood comes into contact with surfaces (for example in a heart-lung machine), as a result of neutralization of the enzymes thereby formed, as well as in disease patterns which lead to activation of the coagulation cascade, for example immunocomplexes, such as occur in connection with chronic, chiefly rheumatic diseases. C1 inactivator is the medicament of choice for hereditary angioedema.

There are a number of processes for the preparation of C1 inactivator from human plasma. Besides multistage processes, for example the method of Haupt, Heimburger et al: Beitrag zur Isolierung und Charakterisierung des C1-Inaktivators aus Humanplasma (Contribution on the isolation and characterization of C1 inactivator from human plasma); Eur. J. Biochem. 17, 254–261 (1970), affinity chromatography is also used (Reboul et al.: A simplified procedure for the purification of C1 inactivator from human plasma; FEBS Letters 79, 45 (1977)). Such processes have certain deficiencies: they are still not simple enough, wasteful and time-consuming. Even ion exchanger chromatography, if necessary combined with gel filtration and affinity chromatography, has not led to the desired success. The process of E. F. Vogelaar et al., Vox. Sang. 26: 118–127 (1974), by which C1 inactivator can be prepared on a large scale for clinical use, does not fulfil the present requirements made of such a product.

It was therefore the object to prepare C1 inactivator by a process which is readily reproducible and leads to a high yield of a highly pure product with a good therapeutic tolerance.

It has now been found, surprisingly, that C1 inactivator is a relatively hydrophilic protein and the proteins which usually accompany C1 inactivator and reduce its specific activity (concomitant proteins) have affinities for hydrophobic groups, in particular aromatic compounds, and that they are thus adsorbed from the C1 inactivator with the aid of such groups fixed to a virtually water-insoluble carrier and can in this manner be separated from the inactivator. Preferred aromatic compounds are phenyl compounds. Suitable carriers are the materials which are known per se, such as those used for hydrophobic chromatography with various active groups. Crosslinked agarose containing aromatic groups which may be bonded via a spacer is preferably used.

Carrier compounds having the following structure are thus suitable for isolating the C1 inactivator:

A—B—Aro., in which A represents the high-molecular, virtually water-insoluble carrier, for example crosslinked agarose, preferably SEPHAROSE ®, and B is an aliphatic bonding member of the aromatic residue preferably a phenyl group, bonded to this carrier. Preferred bonding members, also called spacers, are

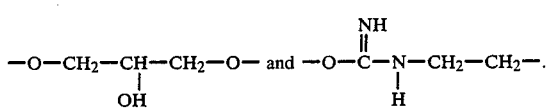

A suitable commercial product of the formula AB—Aro is PHENYL-SEPHAROSE ® CL-4B. Preferred products are products which are similar to this, such as those which can be obtained, for example, by reacting a crosslinked agarose, for example SEPHAROSE ® 4B, with cyanogen bromide and then with an aromatic amine, for example phenylethylamine.

The adsorption of the concomitant proteins of C1 inactivator onto such hydrophobic carriers and their removal from the inactivator is a step which is essential to the invention in the process for the preparation of a pure product and which can, if appropriate, be preceded or followed by process steps which are known per se.

Human plasma is the preferred starting material for isolating C1 inactivator; however, the process step according to the invention can also be applied to other aqueous solutions containing C1 inactivator and concomitant proteins.

The combination of the process step according to the invention and a non-hydrophobic adsorbent, preferably an ion exchanger, especially with diethylaminoethyl groups, is advantageous. Ion exchangers containing QAE groups also lead to a concentration of the C1 inactivator, as do mineral adsorbents, such as, for example, calcium phosphate. Precipitation processes with neutral salts, such as, for example, with ammonium sulfate, are also known and suitable as purification steps for C1 inactivator.

It is essential that therapeutic use of C1 inactivator presents no danger to the patient. The exclusion of transmission of hepatitis is based on the assumption that protein solutions kept at about 60° C. for several hours can no longer transmit hepatitis B even if these solutions contained infectious hepatitis B virus before being warmed. In a further development of the present invention, there was thus the object of providing the product obtained according to the invention in a hepatitis-free form. Solutions containing C1 inactivator can be kept at about 60° C. for several hours with virtually no loss in activity if these solutions contain compounds which stabilize the activity of C1 inactivator. Such compounds are amino acids, sugars and/or sugar alcohols, or mixtures thereof. A solution containing C1 inactivator can be heated at 60° C. with a mixture of 2 moles/liter of glycine and 60% (weight/volume) of sucrose for 10 hours without loss of activity. Generally, amino acids are used in a concentration of 1–3 moles/liter, monosaccharides and oligosaccharides are used in a concentration of 20–60% (weight/volume) and sugar-alcohols are used in a concentration of up to 75% (weight/volume). For the warming procedure, the solution containing C1 inactivator and stabilizer is adjusted to a pH value between 5.5 and 8.5, preferably between 6.5 and 7.5. In addition to glycine, the amino acid preferably used, the following amino acids are also suitable for the stabilization: L-aspartic acid, L-serine, L-valine, L-lysine, L-threonine, L-tyrosine, L-phenylalanine, L-leucine, L-alanine, L-methionine, L-proline, L-hydroxyproline, L-arginine α or β-alanine, glutamine and α-, β- or γ-aminobutyric acid; besides sucrose, the following sugars are suitable; arabinose, glucose, galactose, fructose, ribose, mannose, rhamnose, maltose and raffinose; and the following sugar-alcohols are suitable: erythritol, ribitol, sorbitol and mannitol.

In the presence of the above stabilizing substances, a solution containing C1 inactivator can be warmed at 30° to 100° C. for 1 minute to 48 hours, preferably at 60° C. for 10 hours, in view of the necessity of avoiding transmission of hepatitis.

The invention thus furthermore relates to a process, which comprises heating a C1 inactivator-containing solution in the presence of stabilizers until the solution has lost its infectiousness caused by a content of hepatitis B virus.

Appropriately prepurified material which has been kept, if necessary, at about 60° C. for several hours, contains C1 inactivator and concomitant proteins and has a purity of about 23-25 units of C1 inactivator/mg (specific activity) is treated, according to the invention, in aqueous solution wih an adsorbent A—B—Aro containing hydrophobic substituents, for example PHENYL-SEPHAROSE ®. The concomitant proteins of the C1 inactivator are adsorbed at a weakly acid, neutral to weakly alkaline pH value, preferably at pH 6 to pH 9. The conductivity of the solution is advantageously 60-120 ms. The adsorption step with the hydrophobic carrier material is advantageously combined with a precipitation step for concentration, through which the C1 inactivator is precipitated from the solution. The precipitated C1 inactivator is then redissolved in an aqueous solution containing the precipitant in a concentration at which the C1 inactivator does not precipitate.

If, for example, the C1 inactivator is precipitated with a neutral salt, for example ammonium sulfate, the precipitate can be redissolved in an aqueous solution of a neutral salt in a concentration at which the C1 inactivator remains in solution, for example an ammonium sulfate concentration of 7-14%, directly after the precipitation. By using such a solution, bonding of the conventional proteins accompanying C1 inactivator as an impurity to the hydrophobic carrier is achieved and highly pure C1 inactivator can be separated from the adsorbent, which retains the impurities.

Protein-stabilizing substances which are known per se, for example an amino acid, such as glycine, are added to C1 inactivator for therapeutic use. The product, which is finally purified by hydrophobic chromatography, is sterilized by filtration, adjusted to the desired concentration effective for therapy, filled into containers and, if desired, lyophilized. The amino acid added stabilizes the C1 inactivator during freeze-drying.

A preferred process is performed, for example, as in the following general description, the base substance of C1 inactivator, human plasma, being used here as the starting material:

Human plasma which contains, for example, citrate and is free from cryoglobulins and prothrombin factors is treated with an anion exchanger and the eluate containing C1 inactivator is fractionated with neutral salts. The concomitant proteins of C1 inactivator are adsorbed from most of the other plasma proteins with a hydrophobic adsorbent. A good yield of highly pure C1 inactivator from which concomitant proteins have been removed can thus be isolated in a single step by means of hydrophobic chromatography. C1 inactivator passes a hydrophobic column, for example PHENYL-SEPHAROSE ® in a salt containing solution of appropriate concentration, whereas most of the concomitant proteins, especially ceruloplasmin, which is usually highly concentrated in this fraction, are retained.

If desired, the C1 inactivator in the precipitation residue can be heated at 60° C. for 10 hours, after dissolving in distilled water and adding a sugar, for example sucrose, to the extent of 60% (weight/volume) without substantial loss in activity. After the sucrose has been removed by reprecipitation wih ammonium sulfate from dilute solution, a good yield of highly pure C1 inactivator from which concomitant proteins have been removed can then be isolated immediately, also using the hydrophobic chromatography technique and in a single step.

The example which follows illustrates the invention:

EXAMPLE 1

Deep-frozen citrated plasma which has been cleared of cryoglobulins and from which factor VIII, Cig and human fibrinogen have been isolated, was adsorbed with DEAE-SEPHADEX ® according to P 30 43 857.4, P 30 45 153.7 and P 31 01 752.5 in order to obtain prothrombin concentrate. After the DEAE-SEPHADEX ® had been separated, 10 g of QAE-SEPHADEX ® per liter of plasma were added to the supernatant plasma and the suspension was stirred at 12° C. for 60 minutes; the QAE-adsorbent was then separated and washed with 0.15 molar NaCl.

1.0 molar NaCl, pH 8.0, and 0.0025 mole/liter of EDTA, in a volume of 0.45 liter of buffer per 10 liters of plasma, was used for the elution. The QAE eluate is a deep blue solution which chiefly contains, in addition to ceruloplasmin, C1 inactivator and factor VII. The eluate was fractionated with ammonium sulfate solution at 20° C. 60% saturation was achieved by adding 1,500 ml of saturated ammonium sulfate solution/liter of eluate.

The 60% ammonium sulfate residue in which C1 inactivator was concentrated was then subjected to hydrophobic chromatography on PHENYL-SEPHAROSE ®. For this, the precipitate was redissolved in distilled water to give a solution corresponding to an optical density at 280 nm of ~55, the ammonium sulfate concentration was adjusted to 7% and the pH value was adjusted to 7.2 to 7.6. After clarification and sterilization by filtration, 1.3 liters of this solution were separated on a gel bed with PHENYL-SEPHAROSE ® using a column 31 cm high and 12 cm wide. The first water-clear runnings contained C1 inactivator, well-separated from the ceruloplasmin passing through the column as a blue band. The fraction containing C1 inactivator was concentrated by adding solid ammonium sulfate: 340 g of ammonium sulfate per liter of the fraction running through were added at 6° C. The precipitate was centrifuged off and dissolved in distilled water. The clarification and sterilization by filtration were followed by dialysis against a 1.5% strength glycine buffer. The protein content of C1 inactivator in a portion of the solution was determined with the aid of the radio immuno diffusion technique, and the activity was determined by the method of Lèvy and Lepow (Proc. Soc. Exp. Biol. Med. 101, 608 (1959)), using N-acetyl-L-tyrosine ethyl ester as the substrate. The activity was indicated in C1 inactivator units, 1 U thereby being defined as the amount which inhibited 10 U of C1 esterase. On average, products containing about 40 U of C1 inactivator/mg of C1 inactivator protein were obtained in a yield of 20%, based on the starting plasma. The resulting product was about 90% pure and pyrogen-free and could be used in animal experiments without secondary effects and in the therapy of angioedema.

If desired, it was possible to dissolve the 60% ammonium sulfate precipitation residue in distilled water, to add 60% weight/volume of sucrose, to adjust the pH to 7–7.5 and to heat the mixture at 60° C. for 10 hours. After cooling, the solution was diluted 1:5 with distilled water and precipitated again by adding saturated ammonium sulfate solution up to 60% saturation in order to remove the sucrose. This procedure was followed by hydrophobic chromatography.

We claim:

1. A process for purifying an inactivator of C1 esterase of the complement system (C1 inactivator) comprising subjecting an aqueous solution containing C1 inactivator and concomitant proteins to precipitation and adsorption, wherein an amount of a carrier containing a hydrophobic group effective for adsorbing said concomitant proteins is utilized as an adsorbent, to provide purified C1 inactivator in said aqueous solution.

2. The process of claim 1, wherein said hydrophobic group is an aromatic compound.

3. The process of claim 2, wherein said aromatic compound is a phenyl compound.

4. The process of claim 1, wherein said carrier has the structure A—B—Aro, wherein A is a high molecular, substantially water-insoluble carrier, B is an aliphatic bonding member of the Aro residue; and Aro is a phenyl group.

5. The process of claim 4, wherein A is crosslinked agarose and B is selected from the group consisting of

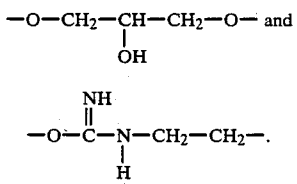

6. The process of claim 1 which comprises: the further step of rendering said C1 inactivator hepatitis-free, prior to subjecting said solution to precipitation and adsorption, by heating said solution in the presence of an amount effective to stabilize the activity of C1 inactivator of a stabilizer selected from the group consisting of an amino acid, a sugar, a sugar alcohol and mixtures thereof at a temperature and for a time sufficient to eliminate infectiousness caused by hepatitis B virus.

7. The process of claim 6, which comprises the further steps of adding an amount effective to stabilize the activity of C1 inactivator of a protein stabilizing substance to said solution of purified C1 inactivator; and lyophilizing said solution of stabilized, purified C1 inactivator.

8. The process of claim 7 wherein said protein stabilizing substance is a sugar.

9. The process of claim 8 wherein said sugar is sucrose.

10. The process of claim 1 which additionally comprises lyophilizing said purified C1 inactivator.

11. The process of claim 1 which comprises the further steps of adding an amount effective to stabilize the activity of C1 inactivator of a stabilizing substance to said solution of purified C1 inactivator; and lyophilizing said solution of stabilized, purified C1 inactivator.

12. The process of claim 11 wherein said protein stabilizing substance is a sugar.

13. The process of claim 12 wherein said sugar is sucrose.

14. A process for isolating an inactivator of C1 esterase of the complement system (C1 inactivator) from an aqueous solution containing said C1 inactivator and also containing proteins having an affinity for hydrophobic groups, which process comprises contacting said aqueous solution with an adsorbent comprising a water-insoluble carrier containing a hydrophobic group in an effective amount sufficient to adsorb said proteins, and separating said aqueous solution containing C1 inactivator from said adsorbent.

15. The process of claim 14, wherein said aqueous solution is human plasma.

16. The process of claim 14, wherein the C1 inactivator is precipitated from said aqueous solution with a neutral salt and redissolved to form an aqueous solution prior to contacting with said adsorbent.

17. The process of claim 14, wherein said aqueous solution has a pH value of from about 5.5 to 8.5.

18. The process of claim 14, wherein said aqueous solution is warmed at about 30° C. to about 100° C. for from about 1 minute to 48 hours.

* * * * *